United States Patent
Abu Khabar

(10) Patent No.: US 9,017,965 B2
(45) Date of Patent: Apr. 28, 2015

(54) HYBRID 3' UNTRANSLATED REGIONS SUITABLE FOR EFFICIENT PROTEIN EXPRESSION IN MAMMALIAN CELLS

(75) Inventor: Khalid S. Abu Khabar, Riyadh (SA)

(73) Assignee: King Faisal Specialist Hospital & Research Centre, Riyadh (SA)

( * ) Notice: Subject to any disclaimer, the term of this patent is extended or adjusted under 35 U.S.C. 154(b) by 1728 days.

(21) Appl. No.: 12/097,169

(22) PCT Filed: Dec. 12, 2005

(86) PCT No.: PCT/EP2005/013316
§ 371 (c)(1),
(2), (4) Date: Sep. 22, 2008

(87) PCT Pub. No.: WO2007/068265
PCT Pub. Date: Jun. 21, 2007

(65) Prior Publication Data
US 2009/0181427 A1    Jul. 16, 2009

(51) Int. Cl.
*C12N 15/63* (2006.01)
*C12N 15/85* (2006.01)

(52) U.S. Cl.
CPC ....................................... *C12N 15/85* (2013.01)

(58) Field of Classification Search
CPC ........................................................ C12N 15/85
USPC ................................................ 536/23.1, 24.1
See application file for complete search history.

(56) References Cited

FOREIGN PATENT DOCUMENTS

WO    WO 2005/095615    10/2005

OTHER PUBLICATIONS

Tatsuka & Mitsui in "Elongation factor-1 alpha gene determines susceptibility to transformation" (Nature, 1992, vol. 359, pp. 333-336).*
Lu & Werner in "The complete cDNA sequence of mouse elongation factor 1 alpha (EF 1 alpha) mRNA" (NAR, 1989, vol. 17, p. 442).*
Eisenberg, E. et al., "Human housekeeping genes are compact," *Trends in Genetics*, 2003, vol. 19, No. 7, pp. 362-365.
Provost, P.R. et al., "Length increase of the human α-globin 3'-untranslated region disrupts stability of the pre-mRNA but not that of the mature mRNA," *Journal of Biological Chemistry*, 2000, vol. 275, pp. 30248-30255.
Qin, H. et al., "The 3'-end of the human β-actin gene enhances activity of the β-actin expression vector system: construction of improved vectors," *Journal of Biochemical and Biophysical Methods*, 1997, vol. 36, No. 1, pp. 63-72.
Tanguay, R.L. et al., "Translational efficiency is regulated by the length of the 3' untranslated region," *Molecular and Cellular Biology*, 1996, vol. 16, No. 1, pp. 146-156.
Wilson, G.M. et al., "An episomal expression vector system for monitoring sequence-specific effects on mRNA stability in human cell lines," *Plasmid*, 1995, vol. 33, No. 3, pp. 198-207.

* cited by examiner

*Primary Examiner* — Catherine Hibbert
(74) *Attorney, Agent, or Firm* — Saliwanchik Lloyd & Eisenschenk

(57) ABSTRACT

The present invention describes the use of hybrid short 3' untranslated (3'UTR) regions which are composed of two regions, one region from an 3' untranslated region of a stable eukaryotic mRNA, and another region from the downstream end of an 3' untranslated region of another eukaryotic mRNA that contains a polyadenylation (polyA) signal. The use of such hybrid regions allows for an efficient protein expression when used in conjunction with circular or linear expression DNA molecules. The present invention provides a recombinant DNA that is composed of a promoter, a protein coding region, and the hybrid 3'UTR in a continuous and directional orientation. The efficient expression systems of the invention are suitable for the economical and efficient production of therapeutic proteins and for use with both transient and stable expression systems.

19 Claims, 4 Drawing Sheets

A  Original vector construct

B  EGFP control construct

Figure 2
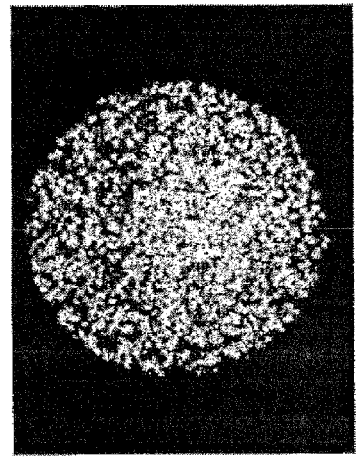
A
Total fluorescence = 85,300,000
Unit: total pixel intensity
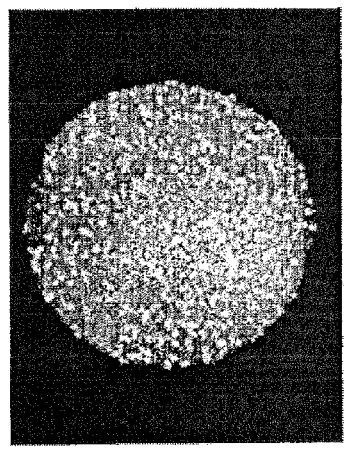
B
Total fluorescence = 231,400,000
Unit: total pixel intensity

Figure 4
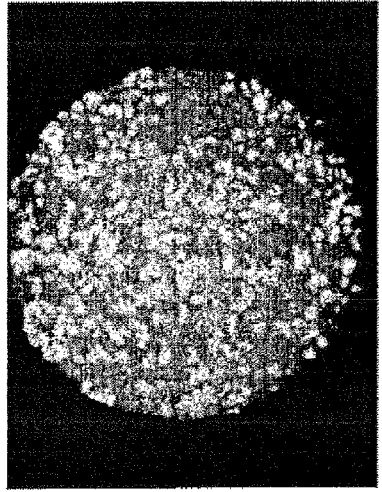
B
Total intensity = 167,000,000
Unit: total pixel intensity
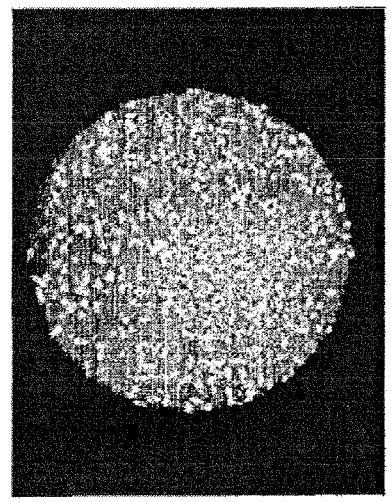
A
Total intensity = 129,000,000
Unit: total pixel intensity

SEQUENCE LISTING

```
<160> NUMBER OF SEQ ID NOS: 3

<210> SEQ ID NO 1
<211> LENGTH: 31
<212> TYPE: DNA
<213> ORGANISM: Artificial Sequence
<220> FEATURE:
<223> OTHER INFORMATION: forward primer with BamHI site

<400> SEQUENCE: 1
gcaccggatc caatattatc cctaatacct g                                    31
```

-continued

```
<210> SEQ ID NO 2
<211> LENGTH: 28
<212> TYPE: DNA
<213> ORGANISM: Artificial Sequence
<220> FEATURE:
<223> OTHER INFORMATION: reverse primer with XbaI site

<400> SEQUENCE: 2
gccagtctag aataacttaa aactgcca                                          28

<210> SEQ ID NO 3
<211> LENGTH: 476
<212> TYPE: DNA
<213> ORGANISM: Artificial Sequence
<220> FEATURE:
<223> OTHER INFORMATION: recombinant hybrid 3 'UTR

<400> SEQUENCE: 3
ggatccaaat attatcccta atacctgcca ccccactctt aatcagtggt ggaagaacgg        60
tctcagaact gtttgtttca attggccatt taagtttagt agtaaaagac tggttaatga       120
taacaatgca tcgtaaaacc ttcagaagga aaggagaatg ttttgtggac cactttggtt       180
ttcttttttg cgtgtggcag ttttaagtta ttctctagag atctgtgtgt tggttttttg       240
tggatctgct gtgccttcta gttgccagcc atctgttgtt tgcccctccc ccgtgccttc       300
cttgaccctg gaaggtgcca ctcccactgt cctttcctaa taaaatgagg aaattgcatc       360
gcattgtctg agtaggtgtc attctattct gggggtggg gtggggcagc acagcaaggg       420
ggaggattgg gaagacaata gcaggcatgc tggggatgcg gtgggctcta tgggta          476
```

HYBRID 3' UNTRANSLATED REGIONS SUITABLE FOR EFFICIENT PROTEIN EXPRESSION IN MAMMALIAN CELLS

FIELD OF INVENTION

The field of invention is expression vector engineering, mammalian protein expression, recombinant DNA technology, and expression of therapeutic proteins.

BACKGROUND OF INVENTION

Eukaryotic messenger RNA (mRNA) contains three regions, 5' untranslated region (5'UTR), protein coding region, and 3' untranslated region (3'UTR). The 3'UTR is the sequence towards the 3' end of the mRNA and contains a polyadenylation signal and a polyadenylation site. The 3'UTR is an important regulatory element in many instances it dictates the mRNA stability and it can also regulate translation efficiency. For example, AU-rich elements tend to destabilize mRNAs (Dalphin et al. 1999). The mRNAs can be classified into three categories based on their half-life: (a) unstable mRNAs with a short half life, for example, less than 2 hours, and (b) intermediately stable mRNAs with a half life that exceeds, for example, 2 hours, and (c) stable mRNAs with a half life that exceeds 8 hours. Many of the housekeeping genes tend to code for stable mRNAs, such as but not limited to globin mRNAs (Chen and Shyu 1994; Shaw and Kamen 1986), β-actin, ribosomal proteins, and glyceraldehyde 3-phosphate dehydrogenase (GAPDH).

Expression vectors are important research and biotechnology tools. In research they are used to study protein function while in industry they are used to produce (therapeutic) proteins. Optimization of expression vectors for efficient protein production has been sought and practiced in many ways, mostly by optimizing strong promoters that lead to an efficient transcription of the mRNA encoded by the protein coding region in the expression vector. Examples of these are the CMV immediate early promoter, SV40 promoter, elongation factor (EF) promoter, and chicken β-actin promoter (Foecking and Hofstetter 1986; Kobayashi et al. 1997).

Likewise, strong polyA signal cassettes were also used to augment the protein expression by providing strong polyadenylation signals that stabilize mRNAs which are produced from the expression vectors. Among the widely used polyA signals are the bovine growth hormone (bGH) polyA signal (U.S. Pat. No. 5,122,458 by Post et al.: Use of a bGH GNA polyadenylation signal in expression of non-bGH polypeptides in higher eukaryotic cells) and SV40 polyA signal (Goodwin and Rottman 1992). Unlike termination signals in bacteria, where the 3' end of the mRNA is formed by the NA polymerase that is simply dropping off the DNA and ceasing transcription, in eukaryotes cleavage occurs that is followed by binding of the polyadenylation complex to an AAUAAA sequence near the end of the mRNA. This complex contains an endonuclease that cuts the RNA about 14-30 bases downstream of the AAUAAA sequence and a polymerase that adds a string of polyA forming the polyA tail (Wigley et al. 1990).

Since the 3' UTR and polyA signal context sequence may influence nuclease degradation of plasmid DNA vectors particularly after delivery and during trafficking to the nucleus, a novel approach that circumvents this problem is described. In this invention, an approach to further optimize expression of proteins is described which uses a hybrid 3'UTR downstream of the protein coding region that consists of two regions, wherein one region is from an 3'UTR of a stable mRNA and the other region is a poly A signal containing region from an 3'UTR of another mRNA.

SUMMARY OF INVENTION

The present invention describes the construction of hybrid short 3' untranslated (3'UTR) regions for use in mammalian expression vectors to boost the expression of proteins encoded in these vectors. The hybrid short 3'UTR comprises two regions that are near each other, i.e. in proximity to each other or adjacent to each other or overlapping with each other or one encompasses the other, one region from an 3' untranslated region of a stable eukaryotic NA, and another region from the downstream end of an 3' untranslated region of a stable eukaryotic mRNA which contains the polyadenylation signal. The first region does not contain a polyadenylation signal, whereas the second region contains a polyadenylation signal and is derived from the downstream end of an 3' untranslated region of a stable eukaryotic mRNA.

In a preferred embodiment, the first region or the two regions comprise the 3'UTR or part of the 3'UTR of the human eukaryotic translation elongation factor 1 alpha 1 EEF1A1).

The present invention further provides a recombinant DNA that is composed of promoter, protein coding region, and the hybrid 3'UTR, in a continuous and directional orientation.

BRIEF DESCRIPTION OF FIGURES

FIG. 2. GFP fluorescence due to protein expression in HEK 293 cells using the unmodified vector (A) and vector containing the hybrid 3'UTR (B).

FIG. 4. GFP fluorescence due to protein expression in HEK 293 cells using the unmodified vector (A) and linear DNA containing the hybrid 3'UTR in form of a PCR product (B).

DETAILED DESCRIPTION OF INVENTION

Figure 1:
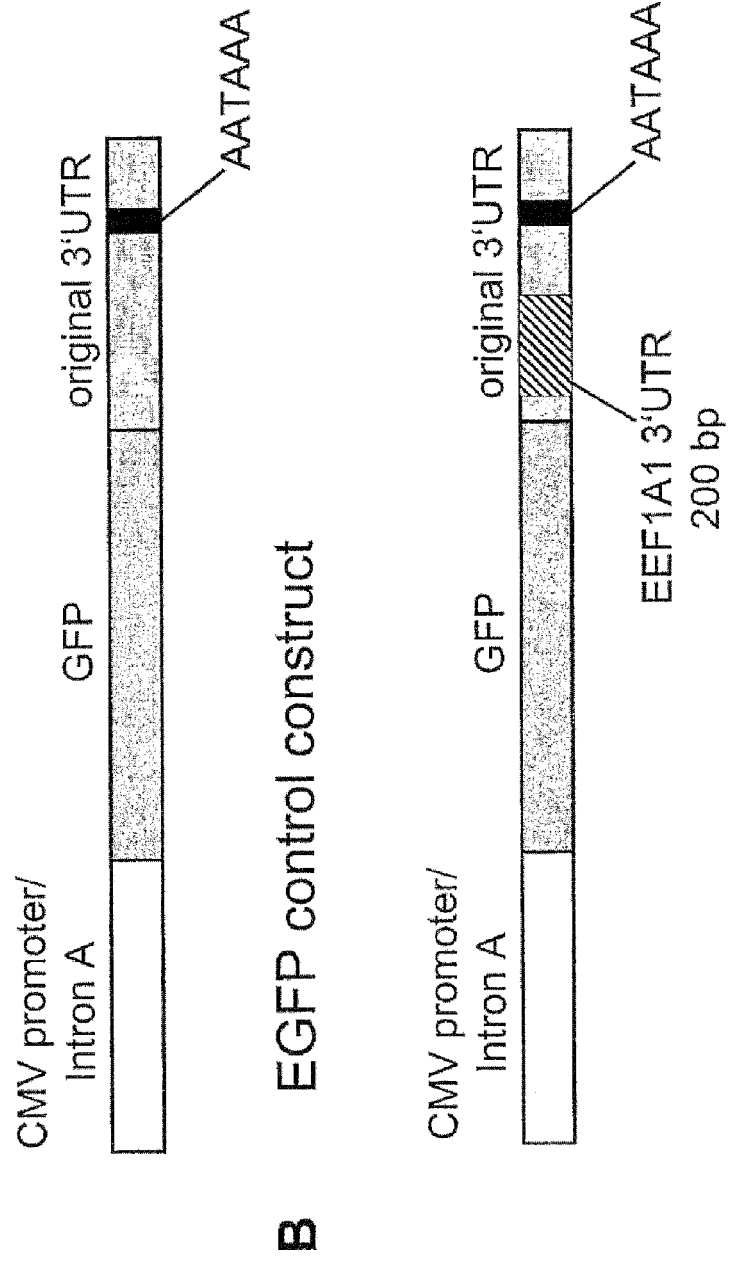
FIG. 1. Construction of the hybrid 3'UTR construct. A vector containing CMV/Itron A promoter, a coding region for green fluorescence protein (GFP), followed by an 3'UTR containing an eukaryotic polyadenylation signal (AATAAA), is modified to include part of the 3'UTR of the human housekeeping gene, human eukaryotic translation elongation factor 1 alpha 1 (EEF1A1). The EEF1A region was cloned into the original 3'UTR region using restriction site cloning and the result is a hybrid 3'UTR region. The upper panel A shows the original construct and the lower panel B shows the new construct with the hybrid 3'UTR.

As discussed above, there is a need to improve and optimize protein expression. Therefore, the problem to be solved by this invention, was to further improve and optimize protein expression systems, such as by improving and optimizing the engineering of expression vectors and/or of their components.

The problem is solved by the present invention by providing a recombinant nucleic acid that comprises a first and a second nucleic acid region, wherein
(a) said first region is derived from an 3' untranslated region (3'UTR) of a stable eukaryotic mRNA,
(b) said first region does not contain a polyadenylation signal, (c) said second region is derived from the downstream end of an 3, untranslated region of another or the same stable eukaryotic mRNA as in (a), and (d) said second region contains a polyadenaylation signal.

With the proviso that said first and second nucleic acid regions when taken together form a hybrid 3'UTR, said hybrid 3'UTR being different from its naturally occurring, i.e. original, counterpart. This proviso means, for example, when said first region is derived from the upstream end of a 3'-UTR of a stable eukaryotic mRNA and said second region is derived from the downstream end of the 3'UM of the same stable eukaryotic mRNA, the hybrid 3'UTR is different from the naturally occurring, i.e. original, 3'UTR.

By "nucleic acid" is meant a single-stranded or double-stranded chain of two or more nucleotide bases including, without limitation, deoxyribonucleic acid (DNA), ribonucleic acid (RNA), and analogs of either DNA or RNA, mRNA, and cDNA, such as PNA. The recombinant nucleic acid of the present inventions are preferably DNA, RNA, or PNA.

By the term a region is "derived from" an 3' untranslated region (3'-UTR) of a stable eukaryotic mRNA is meant that the region is the 3'UTR itself is a part of said 3'UTR or a sequence of the 3'UTR comprising mutations, deletions, truncations, insertions and/or single nucleotide polymorphisms (SNPs).

In a preferred embodiment recombinant nucleic acids are provided, wherein said first region and said second region of the recombinant nucleic acid are in proximity to each other or wherein said first region and said second region are adjacent to each other or wherein said first region and said second region overlap with each other or wherein one region encompasses the other region.

Preferred proximities of the first and second region, i.e. distances between the first and second region, are in the range of 0 to 500 nucleotides, more preferred in the range of 0 to 250 nucleotides and most preferred in the range of 0 to 100 nucleotides.

It is preferred that the 3, end of the first region is adjacent to the 5' end of the second region or that the 3' end of the second region is adjacent to the 5' end of the first region.

It is further preferred that the first region is located with the second region, wherein the first region is preferably located upstream of the polyadenylation signal of the second region.

It is preferred that at least one of the regions is derived from stable mRNAs, such as those of housekeeping genes which exist in abundant amounts inside the cells. As already defined above, stable mRNAs are mRNAs with a half life that exceeds 8 hours.

Preferred housekeeping and/or stable mRNAs are, but are not limited to β-actin, α- and β-globins, glyceraldehyde 3-phosphate dehydrogenase (GAPDH), growth hormone, eukaryotic translation elongation factor 1 alpha 1 (EEF1A1), and many of the ribosomal proteins. Other housekeeping genes are known in the art, see for example Eisenberg and Levanon 2003. It is preformed that the first region and/or the second region is derived from the 3'UTR of housekeeping genes that are abundant (see Table 1).

Since the length of the 3'UTR of housekeeping genes is generally shorter, see Eisenberg and Levanon, 2003, which is also the result of our analysis, see Example 1, the preferred length of the total hybrid 3'UTR according to the invention is less than 1000 nucleotides, preferably less than 500 nucleotides.

In a preferred embodiment the first region is derived from the 3'UTR of eukaryotic translation elongation factor 1 alpha 1 (EEF1A1), see also FIG. 1 and Table 2. In a more preferred embodiment the first region is the 3'UM of eukaryotic translation elongation factor 1 alpha 1 (EEF1A1) or a part thereof.

In another preferred embodiment the first and the second region is derived from the 3'UTR of eukaryotic translation elongation factor 1 alpha 1 (EEF1A1).

In another preferred embodiment, the first region is derived from the 3'UTR of EEF1A1 and the second region is derived from 3'UTR of bovine growth hormone (bGH), preferably a smaller region of the bovine growth hormone 3'UTR that ter contains an efficient polyadenylation signal.

In another aspect of the present invention a recombinant nucleic acid is provided that comprises a first and a second nucleic acid region, wherein both regions are derived from the 3'UTR of the same stable eukaryotic mRNA, preferably from the 3'UTR of eukaryotic translation elongation factor 1 alpha 1 (EEF1A1) or a part thereof. Furthermore, in this aspect of the present invention the above stated proviso does not apply. In a preferred embodiment of this aspect of the present invention the first or second region is identical to the 3'UTR of EEF1A1 or one or more parts thereof. In another preferred embodiment of this aspect of the present invention the first and second region when taken together are identical to the 3'-UTR of EEF1A1 or one or more parts thereof.

The problem is further solved by the present invention by providing a further recombinant nucleic acid comprising the following components in 5, to 3' direction:
(i) a promoter sequence,
(ii) a protein coding region sequence, and
(iii) the hybrid 3'UTR of the present invention as defined above, which is operably lined to the protein coding sequence of (ii).

In another aspect of the present invention the further recombinant nucleic acid comprises the following components in 5' to 3' direction:
(i) a promoter sequence,
(ii) a protein coding region sequence, and
(iii) the 3'UTR of EEF1A1 or parts thereof as defined above, which is operably linked to the protein coding sequence of (ii).

By "operably linked" is meant that the nucleic acid sequence encoding a protein of interest and (transcriptional) regulatory sequences, such as the 3'UTR, are connected in such a way as to permit expression of the nucleic acid sequence in vivo, such as when introduced into a cell. Preferably, the hybrid 3'UTR of the present invention is operably lined to the protein coding sequence in a continuous (uninterrupted) and directional orientation, such as adjacent to the protein coding sequence.

In a preferred embodiment the recombinant nucleic acid of the invention is a linear DNA molecule. Such linear DNA molecules are preferably generated by PCR using at least two primers that specifically hybridize to regions near the 5' end and specifically hybridize to regions near the 37 end of said nucleic acid which is comprised in an expression vector.

The problem is further solved by the present invention by providing an expression vector comprising the nucleic acid according to the present invention.

It is preferred that the expression vector further comprises a selection marker. Selection markers are known in the art however, preferred selection markers are neomycin resistance gene and blasticidin resistance gene.

The protein coding sequences are either coding for a reporter gene or more preferably a therapeutic protein. Preferred reporter genes are GFP, luciferase, or other reporter genes known in the art. Preferred therapeutic proteins are interferones, growth factors, anti-angiogenesis proteins, apoptosis modulating proteins, tumor growth factors or spread suppressing factors, vaccines, recombinant antibodies, or any other current or future therapeutic protein.

The nucleic acids according to the present invention are preferably produced in linear form by a method that comprises the following steps of
(a) providing an expression vector comprising a nucleic acid according to the present invention, wherein said nucleic acid comprises the following components in 57 to 3' direction:
 (i) a promoter sequence,
 (ii) a protein coding region sequence, and
 (iii) the hybrid 3'UTR of the present invention as defined above, which is operably linked to the protein coding sequence of (ii),
(b) providing at least two primers, wherein one primer specifically hybridizes to regions near the 5, end of the nucleic acid according to the present invention, and
wherein the other primer specifically hybridizes to regions near the 3' end of the nucleic acid according to the present invention,
wherein said nucleic acid comprises the following components in 5, to 3' direction:
 (i) a promoter sequence,
 (ii) a protein coding region sequence, and
 (iii) the hybrid 3'UTR of the present invention as defined above, which is operably linked to the protein coding sequence of (ii),
(c) performing a PCR, and
(d) obtaining the amplification product of step (c).

In another aspect of the invention the nucleic acids according to the present invention are preferably produced in linear form by a method that comprises the following steps of
(a) providing an expression vector comprising a nucleic acid according to the present invention, wherein said nucleic acid comprises the following components in 5' to 3, direction:
 (i) a promoter sequence,
 (ii) a protein coding region sequence, and
 (iii) the 3'UTR of EEF1A1 or parts thereof as defined above, which is operably linked to the protein coding sequence of (ii),
(b) providing at least two primers, wherein one primer specifically hybridizes to regions near the 5' end of the nucleic acid according to the present invention, and wherein the other primer specifically hybridizes to regions near the 3' end of the nucleic acid according to the present invention,
wherein said nucleic acid comprises the following components in 5' to 37 direction:
 (i) a promoter sequence,
 (ii) a protein coding region sequence, and
 (iii) the 3'UTR of EEF1A1 or parts thereof as defined above, which is operably linked to the protein coding sequence of (ii)
(c) performing a PCR, and
(d) obtaining the amplification product of step (c).

The problem is further solved by the present invention by providing a host cell characterized in that it contains the expression vector of the present invention or the recombinant linear nucleic acid of the present invention, and further characterized in that it transiently or stably expresses the protein encoded in the expression vector of the present invention or the recombinant linear nucleic acid of the present invention.

Transient and stable expression of proteins is known in the art. When proteins are expressed transiently a foreign gene that codes for the particular protein is expressed by recipient/host cells over a relatively brief time span, wherein the gene is not integrated into the genome of the host cell, whereas in case of stable expression of proteins the foreign coding gene is integrated into the genome of the host cell.

The host cells of the present invention are preferably obtained by in vivo injection of the expression vector of the present invention or the recombinant linear nucleic acid of the present invention into cells.

A preferred method for obtaining a host cell of the present invention comprises the following steps of
(a) providing an expression vector of the present invention or a recombinant linear nucleic acid of the present invention,
(b) in vivo injection of the expression vector of the present invention or the recombinant linear nucleic acid of the present invention into cells,
(c) obtaining the injected cells of step (b).

Suitable cells are known in the art. However, preferred cells are HEK 293, HeLa, Huh7, COS-7, and CHO cell lines.

A preferred embodiment is a method for expressing proteins, comprising providing and culturing of host cells of the present invention, under conditions allowing transient or stable expression of proteins, and obtaining said expressed proteins.

Culturing conditions of cells and cell culturing conditions that allow the expression of proteins are known in the art. Preferred conditions are at temperature of about 37° C. and a humidified atmosphere, a medium containing buffers with a salt concentration and a pH1 suitable for mammalian cell culture.

The proteins can be either expressed in a secreted form or in cellular compartments. The expressed proteins can further be obtained by methods for isolating and purifying proteins from cells, which are known in the art. Preferred methods for purification are affinity chromatography, immuno-affinity chromatography, protein precipitation, buffer exchanges, ion-exchange chromatography, hydrophobic interaction chromatography, size-exclusion chromatography and electrophoresis-based purification.

Mammalian expression vectors are powerful research and industrial biotechnology tools. They comprise as a minimum requirement an eukaryotic promoter, a protein coding sequence, and an 3'UTR that contains an efficient polyadenylation signal. Many attempts of enchancing protein expression from vectors have been focused on promoters. In this invention, enhanced efficiency of protein expression was achieved by modifying the 3'-UTR that is continuously and directionally operable linked to the protein coding sequence.

The 3'UTRs which include the polyadenylation signal and upstream and downstream polyadenylation context sequences can be rendered efficient by making a hybrid 3'UTR consisting of two regions: a first region from an 3' untranslated region of a stable eukaryotic mRNA that does not contain a polyadenylation signal, and a second region from the downstream end of an 3' untranslated region of a stable eukaryotic mRNA that contains a polyadenylation signal.

The sequences can be obtained by amplification of the said region from the 3'UTR of the housekeeping mRNA using RT-PCR utilizing two primers specific to the region of interest. These PCR products are ten cloned into a vector, such as a plasmid or viral vector, which contains already the second region. Preferred examples for vectors are pUC 19 based plasmids, pcDNA3.1, Gwiz, CMVSport, etc. which are available from different research tool companies, such as invitrogen, Clontech, Strategene and Gene Therapy Systems, inc. There are different preferred ways of cloning, such as restriction site-directed cloning, blunt cloning, or recombination-based cloning. The hybrid USR can preferably be created by conventional cloning techniques involving restriction enzyme digestion of commercially available plasmids and cDNA molecules, or can be synthesized using PCR or an automated DNA synthesizer using methods known in the art.

It has been shown that a large fraction of human polyadenylation sites is flanked by U-rich elements, both upstream and downstream of the cleavage site, located around positions 0 to −50 and +20 to +60, relative to the polyA signal (Legendre and Gautheret 2003) Thus, it is likely that the enhanced efficiency of protein expression which is achieved by the present invention is caused by the presence of additional strong upstream sequences in the 3'UTR of EEF1A1.

Once the expression vectors containing the hybrid molecules are generated they can be transfected into cells by any known transfection method. Alternatively, linear fragments can be generated by PCR or synthesized genes that contain the minimum linear cassette containing the promoter, coding region, and the hybrid 3'UTR.

EXAMPLES

The following examples are intended for illustration purposes only, and should not be construed as limiting the scope of the present invention in any way.

Example 1

We used the list of housekeeping genes that were identified by Eisenberg and Levanon (2003) based on constitutive expression in all tissues. We assumed that a housekeeping gene with an abundance of more than 1000 ESTs (total number of expressed sequence tags in EST database per expressed genes) is stable because abundant transcripts are likely to be associated with stable mRNAs. The abundance data were obtained from the dbEST, a database of expressed sequence tags that is publicly available in the National Center for Biotechnology Information (NCBI, USA). Table 1 below shows the list of these abundant housekeeping genes and this list also constitutes the preferred sequence data source for the hybrid 3'UTR used in this invention. When compared to our list of unstable mRNA (derived from AU-rich mRNA which tend to code for unstable mRNAs), we found different statistical differences. The average abundance of housekeeping mRNAs was 1151±78 (SEAM n=570), i.e. higher than those of unstable mRNAs (by 5-fold) which had an average abundance of 220±16 (n=266). The average length of the 3'UTR of stable mRNAs appears shorter than those of unstable mRNAs (AU-rich mRNAs). The average length of 3'UTR of the housekeeping mRNA was 676±30 nucleotides (SEM, n±572) while the average length of the 3'UTR of abundant housekeeping mRNA, i.e., those with more than 1000 ESTs, was 570±50 nucleotides (SEM, n=178). In contrast, the average length of unstable AU-rich mRNAs was more than 1560±39 nucleotides (SEM, n=1027).

TABLE 1

List of Abundant Housekeeping Genes

| Acc | Definition | Symbol[a] | Length[b] | Abundance[c] |
| --- | --- | --- | --- | --- |
| NM_001402 | Eukaryotic translation elongation factor 1 alpha 1 | EEF1A1 | 387 | 20011 |
| NM_001614 | Actin, gamma 1 | ACTG1 | 718 | 16084 |
| NM_002046 | Glyceraldehyde-3-phosphate dehydrogenase | GAPD | 201 | 15931 |
| NM_001101 | Actin, beta | ACTB | 593 | 15733 |
| NM_000967 | Ribosomal protein L3 | RPL3 | 74 | 10924 |
| NM_006082 | Tubulin, alpha, ubiquitous | K-ALPHA-1 | 174 | 10416 |
| NM_001428 | Enolase 1, (alpha) | ENO1 | 357 | 9816 |
| NM_006098 | Guanine nucleotide binding protein (G protein), beta polypeptide 2-like 1 | GNB2L1 | 45 | 8910 |
| NM_002032 | Ferritin, heavy polypeptide 1 | FTH1 | 138 | 8861 |
| NM_002654 | Pyruvate kinase, muscle | PKM2 | 643 | 7413 |
| NM_004048 | Beta-2-microglobulin | B2M | 568 | 7142 |
| NM_006597 | Heat shock 70 kDa protein 8 | HSPA8 | 258 | 6066 |
| NM_000034 | Aldolase A, fructose-bisphosphate | ALDOA | 252 | 5703 |
| NM_021009 | Ubiquitin C | UBC | 67 | 5579 |
| NM_006013 | Ribosomal protein L10 | RPL10 | 1,503 | 5572 |
| NM_012423 | Ribosomal protein L13a | RPL13A | 509 | 5552 |
| NM_007355 | Heat shock 90 kDa protein 1, beta | HSPCB | 309 | 5436 |
| NM_004046 | ATP synthase, H+ transporting, mitochondrial F1 complex, alpha subunit, isoform 1, cardiac muscle | ATP5A1 | 164 | 5434 |
| NM_000516 | GNAS complex locus | GNAS | 362 | 4677 |
| NM_001743 | Calmodulin 2 (phosphorylase kinase, delta) | CALM2 | 611 | 4306 |
| NM_005566 | Lactate dehydrogenase A | LDHA | 566 | 4186 |
| NM_000973 | Ribosomal protein L8 | RPL8 | 92 | 4042 |
| NM_002948 | Ribosomal protein L15 | RPL15 | 1,368 | 3861 |
| NM_000977 | Ribosomal protein L13 | RPL13 | 424 | 3774 |
| NM_002952 | Ribosomal protein S2 | RPS2 | 86 | 3758 |
| NM_005507 | Cofilin 1 (non-muscle) | CFL1 | 508 | 3616 |
| NM_004039 | Annexin A2 | ANXA2 | 294 | 3560 |
| NM_021019 | Myosin, light polypeptide 6, alkali, smooth muscle and non-muscle | MYL6 | 209 | 3512 |
| NM_002300 | Lactate dehydrogenase B | LDHB | 230 | 3501 |
| NM_003217 | Testis enhanced gene transcript (BAX inhibitor 1) | TEGT | 1,847 | 3438 |
| NM_002568 | Poly(A) binding protein, cytoplasmic 1 | PABPC1 | 445 | 3241 |
| NM_001015 | Ribosomal protein S11 | RPS11 | 85 | 3220 |
| NM_003973 | Ribosomal protein L14 | RPL14 | 156 | 3198 |
| NM_000969 | Ribosomal protein L5 | RPL5 | 78 | 3167 |
| NM_007104 | Ribosomal protein L10a | RPL10A | 32 | 3079 |
| NM_001642 | Amyloid beta (A4) precursor-like protein 2 | APLP2 | 1,364 | 3002 |
| NM_001418 | Eukaryotic translation initiation factor 4 gamma, 2 | EIF4G2 | 791 | 2913 |
| NM_002635 | Solute carrier family 25 (mitochondrial carrier; phosphate carrier), member 3 | SLC25A3 | 197 | 2900 |
| NM_001009 | Ribosomal protein S5 | RPS5 | 58 | 2897 |

TABLE 1-continued

List of Abundant Housekeeping Genes

| Acc | Definition | Symbol[a] | Length[b] | Abundance[c] |
|---|---|---|---|---|
| NM_000291 | Phosphoglycerate kinase 1 | PGK1 | 1,016 | 2858 |
| NM_001728 | Basigin (OK blood group) | BSG | 769 | 2827 |
| NM_001658 | ADP-ribosylation factor 1 | ARF1 | 1,194 | 2772 |
| NM_001003 | Ribosomal protein, large, P1 | RPLP1 | 39 | 2770 |
| NM_018955 | Ubiquitin B | UBB | 144 | 2732 |
| NM_005998 | Chaperonin containing TCP1, subunit 3 (gamma) | CCT3 | 255 | 2709 |
| NM_001967 | Eukaryotic translation initiation factor 4A, Isoform 2 | EIF4A2 | 626 | 2693 |
| NM_001469 | Thyroid autoantigen 70 kDa (Ku antigen) | G22P1 | 259 | 2682 |
| NM_000918 | Procollagen-proline, 2-oxoglutarate 4-dioxygenase (proline 4-hydroxylase), beta polypeptide (protein disulfide isomerase; thyroid hormone binding protein p55) | P4HB | 868 | 2659 |
| NM_002574 | Peroxiredoxin 1 | PRDX1 | 323 | 2604 |
| NM_001020 | Ribosomal protein S16 | RPS16 | 78 | 2573 |
| NM_007363 | Non-POU domain containing, octamer-binding | NONO | 1,119 | 2557 |
| NM_001022 | Ribosomal protein S19 | RPS19 | 63 | 2533 |
| NM_001675 | Activating transcription factor 4 (tax-responsive enhancer element B67) | ATF4 | 85 | 2479 |
| NM_005617 | Ribosomal protein S14 | RPS14 | 78 | 2465 |
| NM_001664 | Ras homolog gene family, member A | RHOA | 1,045 | 2426 |
| NM_005801 | Putative translation initiation factor | SUI1 | 836 | 2425 |
| NM_000981 | Ribosomal protein L19 | RPL19 | 80 | 2381 |
| NM_000979 | Ribosomal protein L18 | RPL18 | 49 | 2362 |
| NM_001026 | Ribosomal protein S24 | RPS24 | 77 | 2355 |
| NM_000975 | Ribosomal protein L11 | RPL11 | 53 | 2314 |
| NM_002117 | Major histocompatibility complex, class I, C | HLA-C | 434 | 2278 |
| NM_004068 | Adaptor-related protein complex 2, mu 1 subunit | AP2M1 | 494 | 2230 |
| NM_006429 | Chaperonin containing TCP1, subunit 7 (eta) | CCT7 | 164 | 2216 |
| NM_022551 | Ribosomal protein S18 | RPS18 | 5,538 | 2208 |
| NM_001013 | Ribosomal protein S9 | RPS9 | 73 | 2113 |
| NM_005594 | Nascent-polypeptide-associated complex alpha polypeptide | NACA | 133 | 2075 |
| NM_001028 | Ribosomal protein S25 | RPS25 | 74 | 2066 |
| NM_032378 | Eukaryotic translation elongation factor 1 delta (guanine nucleotide exchange protein) | EEF1D | 76 | 2051 |
| NM_000999 | Ribosomal protein L38 | RPL38 | 50 | 2007 |
| NM_000994 | Ribosomal protein L32 | RPL32 | 64 | 2003 |
| NM_007008 | Reticulon 4 | RTN4 | 973 | 1969 |
| NM_001909 | Cathepsin D (lysosomal aspartyl protease) | CTSD | 834 | 1940 |
| NM_006325 | RAN, member RAS oncogene family | RAN | 892 | 1906 |
| NM_003406 | Tyrosine 3-monooxygenase/tryptophan 5-monooxygenase activation protein, zeta polypeptide | YWHAZ | 2,013 | 1892 |
| NM_006888 | Calmodulin 1 (phosphorylase kinase, delta) | CALM1 | 3,067 | 1880 |
| NM_004339 | Pituitary tumor-transforming 1 interacting protein | PTTG1IP | 1,985 | 1837 |
| NM_005022 | Profilin 1 | PFN1 | 289 | 1787 |
| NM_001961 | Eukaryotic translation elongation factor 2 | EEF2 | 504 | 1754 |
| NM_003091 | Small nuclear ribonucleoprotein polypeptides B and B1 | SNRPB | 295 | 1735 |
| NM_006826 | Tyrosine 3-monooxygenase/tryptophan 5-monooxygenase activation protein, theta polypeptide | YWHAQ | 1,310 | 1726 |
| NM_002140 | Heterogeneous nuclear ribonucleoprotein K | HNRPK | 1,227 | 1725 |
| NM_001064 | Transketolase (Wernicke-Korsakoff syndrome) | TKT | 167 | 1721 |
| NM_021103 | Thymosin, beta 10 | TMSB10 | 317 | 1714 |
| NM_004309 | Rho GDP dissociation inhibitor (GDI) alpha | ARHGDIA | 1,206 | 1702 |
| NM_002473 | Myosin, heavy polypeptide 9, non-muscle | MYH9 | 1,392 | 1692 |
| NM_000884 | IMP (Inosine monophosphate) dehydrogenase 2 | IMPDH2 | 63 | 1690 |
| NM_001004 | Ribosomal protein, large P2 | RPLP2 | 59 | 1688 |
| NM_001746 | Calnexin | CANX | 2,302 | 1677 |
| NM_002819 | Polypyrimidine tract binding protein 1 | PTBP1 | 1,561 | 1663 |
| NM_000988 | Ribosomal protein L27 | RPL27 | 59 | 1660 |
| NM_004404 | Neural precursor cell expressed, developmentally down-regulated 5 | NEDD5 | 2,090 | 1654 |
| NM_005347 | Heat shock 70 kDa protein 5 (glucose-regulated protein, 78 kDa) | HSPA5 | 1,757 | 1651 |
| NM_000175 | Glucose phosphate isomerase | GPI | 296 | 1635 |
| NM_001207 | Basic transcription factor 3 | BTF3 | 300 | 1632 |
| NM_003186 | Transgelin | TAGLN | 405 | 1612 |
| NM_003334 | Ubiquitin-activating enzyme E1 (A1S9T and BN75 temperature sensitivity complementing) | UBE1 | 199 | 1590 |
| NM_001018 | Ribosomal protein S15 | RPS15 | 32 | 1574 |
| NM_003404 | Tyrosine 3-monooxygenase/tryptophan 5-monooxygenase activation protein, beta polypeptide | YWHAB | 2,088 | 1523 |
| NM_003753 | Eukaryotic translation initiation factor 3, subunit 7 zeta, 66/67 kDa | EIF3S7 | 152 | 1509 |
| NM_005762 | Tripartite motif-containing 28 | TRIM28 | 193 | 1507 |
| NM_005381 | Nucleolin | NCL | 284 | 1501 |
| NM_000995 | Ribosomal protein L34 | RPL34 | 450 | 1495 |
| NM_002823 | Prothymosin, alpha (gene sequence 28) | PTMA | 720 | 1462 |
| NM_002415 | Macrophage migration inhibitory factor (glycosylation-inhibiting factor) | MIF | 117 | 1459 |
| NM_002128 | High-mobility group box 1 | HMGB1 | 1,527 | 1457 |

TABLE 1-continued

List of Abundant Housekeeping Genes

| Acc | Definition | Symbol[a] | Length[b] | Abundance[c] |
|---|---|---|---|---|
| NM_006908 | Ras-related C3 botulinum toxin substrate 1 (rho family, small GTP binding protein Rac1) | RAC1 | 1,536 | 1437 |
| NM_002070 | Guanine nucleotide binding protein (G protein), alpha inhibiting activity polypeptide 2 | GNAI2 | 512 | 1435 |
| NM_001997 | Finkel-Biskis-Reilly murine sarcoma virus (FBR-MuSV) ubiquitously expressed (fox derived); ribosomal protein S30 | FAU | 68 | 1428 |
| NM_014390 | Staphylococcal nuclease domain containing 1 | SND1 | 556 | 1422 |
| NM_014764 | DAZ associated protein 2 | DAZAP2 | 1,322 | 1419 |
| NM_005917 | Malate dehydrogenase 1, NAD (soluble) | MDH1 | 208 | 1396 |
| NM_001494 | GDP dissociation inhibitor 2 | GDI2 | 785 | 1395 |
| NM_014225 | Protein phosphatase 2 (formerly 2A), regulatory subunit A (PR 65), alpha isoform | PPP2R1A | 472 | 1391 |
| NM_001660 | ADP-ribosylation factor 4 | ARF4 | 858 | 1382 |
| NM_001823 | Creatine kinase, brain | CKB | 206 | 1381 |
| NM_003379 | Villin 2 (ezrin) | VIL2 | 1,272 | 1380 |
| NM_000182 | Hydroxyacyl-Coenzyme A dehydrogenase/3-ketoacyl-Coenzyme A thiolase/enoyl-Coenzyme A hydratase (trifunctional protein), alpha subunit | HADHA | 647 | 1379 |
| NM_003746 | Dynein, cytoplasmic, light polypeptide 1 | DNCL1 | 281 | 1375 |
| NM_007103 | NADH dehydrogenase (ubiquinone) flavoprotein 1, 51 kDa | NDUFV1 | 103 | 1352 |
| NM_000992 | Ribosomal protein L29 | RPL29 | 164 | 1349 |
| NM_007209 | Ribosomal protein L35 | RPL35 | 35 | 1345 |
| NM_006623 | Phosphoglycerate dehydrogenase | PHGDH | 231 | 1340 |
| NM_002796 | Proteasome (prosome, macropain) subunit, beta type, 4 | PSMB4 | 108 | 1340 |
| NM_002808 | Proteasome (prosome, macropain) 26S subunit, non-ATPase, 2 | PSMD2 | 231 | 1326 |
| NM_000454 | Superoxide dismutase 1, soluble (amyotrophic lateral sclerosis 1 (adult)) | SOD1 | 346 | 1323 |
| NM_003915 | RNA binding motif protein 12 | RBM12 | 216 | 1323 |
| NM_004924 | Actinin, alpha 4 | ACTN4 | 1,099 | 1316 |
| NM_006086 | Tubulin, beta 3 | TUBB3 | 296 | 1314 |
| NM_001016 | Ribosomal protein S12 | RPS12 | 56 | 1304 |
| NM_003365 | Ubiquinol-cytochrome c reductase core protein I | UQCRC1 | 126 | 1303 |
| NM_003016 | Splicing factor, arginine/serine-rich 2 | SFRS2 | 1,059 | 1301 |
| NM_007273 | Repressor of estrogen receptor activity | REA | 332 | 1281 |
| NM_014610 | Glucosidase, alpha; neutral AB | GANAB | 1,652 | 1280 |
| NM_001749 | Calpain, small subunit 1 | CAPNS1 | 514 | 1270 |
| NM_005080 | X-box binding protein 1 | XBP1 | 1,003 | 1269 |
| NM_005216 | Dolichyl-diphosphooligosaccharide-protein glycosyltransferase | DDOST | 616 | 1268 |
| NM_004640 | HLA-B associated transcript 1 | BAT1 | 237 | 1262 |
| NM_021983 | Major histocompatibility complex, class II, DR beta 4 | HLA-DRB1 | 313 | 1251 |
| NM_013234 | Eukaryotic translation initiation factor 3 subunit k | eIF3k | 84 | 1251 |
| NM_004515 | Interleukin enhancer binding factor 2, 45 kDa | ILF2 | 384 | 1249 |
| NM_000997 | Ribosomal protein L37 | RPL37 | 50 | 1244 |
| NM_000801 | FK506 binding protein 1A, 12 kDa | FKBP1A | 1,149 | 1243 |
| NM_000985 | Ribosomal protein L17 | RPL17 | 58 | 1243 |
| NM_001014 | Ribosomal protein S10 | RPS10 | 57 | 1232 |
| NM_001069 | Tubulin, beta 2 | TUBB2 | 194 | 1230 |
| NM_004960 | Fusion (involved in t(12; 16) in malignant liposarcoma) | FUS | 166 | 1197 |
| NM_005165 | Aldolase C, fructose-bisphosphate | ALDOC | 432 | 1195 |
| NM_004930 | Capping protein (actin filament) muscle Z-line, beta | CAPZB | 259 | 1193 |
| NM_000239 | Lysozyme (renal amyloidosis) | LYZ | 1,016 | 1190 |
| NM_007263 | Coatomer protein complex, subunit epsilon | COPE | 263 | 1179 |
| NM_001861 | Cytochrome c oxidase subunit IV isoform 1 | COX4I1 | 129 | 1178 |
| NM_003757 | Eukaryotic translation initiation factor 3, subunit 2 beta, 36 kDa | EIF3S2 | 408 | 1169 |
| NM_005745 | B-cell receptor-associated protein 31 | BCAP31 | 438 | 1166 |
| NM_002743 | Protein kinase C substrate 80K-H | PRKCSH | 337 | 1158 |
| NM_004161 | RAB1A, member RAS oncogene family | RAB1A | 638 | 1115 |
| NM_002080 | Glutamic-oxaloacetic transaminase 2, mitochondrial (aspartate aminotransferase 2) | GOT2 | 1,039 | 1114 |
| NM_005731 | Actin related protein 2/3 complex, subunit 2, 34 kDa | ARPC2 | 448 | 1113 |
| NM_006445 | PRP8 pre-mRNA processing factor 8 homolog (yeast) | PRPF8 | 173 | 1110 |
| NM_001867 | Cytochrome c oxidase subunit VIIc | COX7C | 168 | 1106 |
| NM_002375 | Microtubule-associated protein 4 | MAP4 | 1,164 | 1102 |
| NM_003145 | Signal sequence receptor, beta (translocon-associated protein beta) | SSR2 | 492 | 1099 |
| NM_001788 | CDC10 cell division cycle 10 homolog (S. cerevisiae) | CDC10 | 1,015 | 1094 |
| NM_006513 | Seryl-tRNA synthetase | SARS | 323 | 1085 |
| NM_003754 | Eukaryotic translation initiation factor 3, subunit 5 epsilon, 47 kDa | EIF3S5 | 152 | 1081 |
| NM_005112 | WD repeat domain 1 | WDR1 | 845 | 1080 |
| NM_004893 | H2A histone family, member Y | H2AFY | 635 | 1072 |
| NM_004494 | Hepatoma-derived growth factor (high-mobility group protein 1-like) | HDGF | 1,339 | 1069 |
| NM_001436 | Fibrillarin | FBL | 111 | 1069 |
| NM_003752 | Eukaryotic translation initiation factor 3, subunit 8, 110 kDa | EIF3S8 | 201 | 1060 |
| NM_003321 | Tu translation elongation factor, mitochondrial | TUFM | 207 | 1038 |
| NM_001119 | Adducin 1 (alpha) | ADD1 | 1,569 | 1037 |
| NM_005273 | Guanine nucleotide binding protein (G protein), beta polypeptide 2 | GNB2 | 386 | 1030 |
| NM_006755 | Transaldolase 1 | TALDO1 | 256 | 1026 |

TABLE 1-continued

List of Abundant Housekeeping Genes

| Acc | Definition | Symbol[a] | Length[b] | Abundance[c] |
|---|---|---|---|---|
| NM_023009 | MARCKS-like 1 | MARCKSL1 | 774 | 1014 |
| NM_002799 | Proteasome (prosome, macropain) subunit, beta type, 7 | PSMB7 | 162 | 1012 |
| NM_002539 | Ornithine decarboxylase 1 | ODC1 | 343 | 1009 |
| NM_006801 | KDEL (Lys-Asp-Glu-Leu) endoplasmic reticulum protein retention receptor 1 | KDELR1 | 742 | 1007 |
| NM_014944 | Calsyntenin 1 | CLSTN1 | 1,481 | 1003 |
| NM_007262 | Parkinson disease (autosomal recessive, early onset) 7 | PARK7 | 253 | 1002 |

The above list of the accession number for housekeeping genes was obtained from Eisenberg and Levanon (2003). The accession numbers were used as input for a PERL (Programmed Extraction Report Language) computer program that extracts EST data from the Unigene database. The Unigene database was downloaded as a text file from the NCBI website. The length of the 3'UTR was derived by computationally extracting the 3'UTR (Bakheet al, 2001).
[a] is a commonly used abbreviation of the gene product;
[b] is the length of the 3'UTR;
[c] is the number of ESTs.

Example 2

A standard pUC 19 based expression vector containing green fluorescence protein (GFP) was used, which contains the human cytomegalovirus (CMV) immediate early promoter, the coding region of enhanced GFP (EGFP) gene and 3'UTR of bovine growth hormone, and ter contains the polyA signal. Suitable expression vectors could, for example, be purchased from Invitrogen, Clontech, Invivogen, Gene Therapy Systems, and Promega, Inc. A PCR product derived from a portion of the 3'UTR of the human elongation factor alpha 1, EEF1A, was generated using a forward primer that contains a BamHI restriction site at the 5' terminus of the primer (SEQ ID NO: 1) and a reverse primer that contains a XbaI restriction site at the 5' terminus of the primer (SEQ ID NO: 2). The sequences of the primers are as follows:

```
        BamHI
GCACCGGATCCAATATTATCCCTAATACCTG

XbaI
GCCAGTCTAGAAATAACTTAAAACTGCCA
```

The primers amplify a 210 bp region 1461-1680 in EEF1A which has the accession number NM_001402. The PCR product was cut using restriction enzymes BamHI and XbaI (New England BioLabs, NEB). Briefly, 10 µg of the PCR product was digested with 10 units of XbaI in a buffer containing 0.1 µg/ml BSA for 1 hr at 37° C. followed by digestion with BamHI in BamHI buffer for an additional 1 hr at 37° C.

The digested PCR products were extracted using a phenol/chloroform method followed by ethanol precipitation. The PCR region was cloned into the GFP vector that was previously digested with the same restriction enzymes (BamHI and XbaI) and previously purified using phenol/chloroform extraction and ethanol precipitation. The BamHI and XbaI sites are located downstream of the end of the EGFP coding region and upstream of the polyA signal (FIG. 1A), Cloning of the PCR products into the vector was achieved using a ligation reaction: 30 ng of digested vector DNA is mixed with 90 ng of digested PCR products in a 10 µl reaction containing T4 DNA ligase. The ligated products were used to transform competent DH5α E. coli cells followed by expansion of the resulting colonies in bacterial culture medium. The recombinant DNA was extracted using the Qiagen plasmid purification kit (Qiagen, Germany). The sizes of the vectors harboring the inserts were verified using gel electrophoresis. The size of the vector without the modified 3'UTR is 5757 bases and the size of the vector with the modified 3'UTR is 5933 bases.

The recombinant hybrid 3'UTR sequence (~400 bp) was searched against NCBI human genome databases to search for the best homology and found to contain the following: a portion of the human EEFA1 and a portion of bovine growth hormone bGH) containing polyA signal. The sequence of the entire hybrid 3'UTR is given in Table 2 (SEQ ID NO: 3).

TABLE 2

Sequence of the efficient hybrid 3'UTR ggatccaaatattatccctaatacctgccacccactcttaatcagtggtggaagaacggtc tcagaactgtttgtttcaattggccatttaagtttagtagtaaaagactggttaatgataac aatgcatcgtaaaaccttcagaaggaaaggagaatgttttgtggaccactttggttttcttt tttgcgtgtggcagttttaagttattctctagagatctgtgtgttggttttttgtggatctg ctgtgccttctagttgccagccatctgttgtttgccctccccgtgccttccttgaccctg gaaggtgccactcccactgtcctttcct<u>aataaa</u>atgaggaaattgcatcgcattgtctgag taggtgtcattctattctgggggtggggtggggcagcacagcaaggggaggattgggaag acaatagcaggcatgctgggatgcggtgggctctatgggta The polyA site (AATAAA) is underlined.

The resultant expression vector with the hybrid 3'UTRs were used for functional studies to confirm the expression of the encoded protein, namely GFP. The HEK 293 cell line was used for transfection. HEK293 cells were grown at standard culture conditions (37° C., 5% $CO_2$) in RPMI 1788 medium supplemented with 10% PBS and antibiotics (GIBCO BRL, Gaithersburg, Md.). $3\times10^4$ cells per well in 96-well plates were transfected with 1 µg of the original (unmodified) expression vector or the modified vector. Transfections were performed in serum-free medium using LipofectinAmine 2000 (Gibco) for 5 h, followed by replacing medium with serum-supplemented medium. After approximately 48 hours, the cells were visualized using a fluorescence microscope and the optimal excitation wavelength for GFP of 488 nm and emission wavelength of 503 nm. Images were captured using a camera mounted on top of the microscope. The images were read by an algorithm that quantitates total fluorescence intensities in pixels. FIG. 2 shows exemplary images and the fluorescence results of these images. The modified vector, i.e. the vector with the hybrid 3'UTR, resulted in an approximately 3-fold increase in the protein expression as evaluated by the GFP expression.

Example 3

Figure 3:
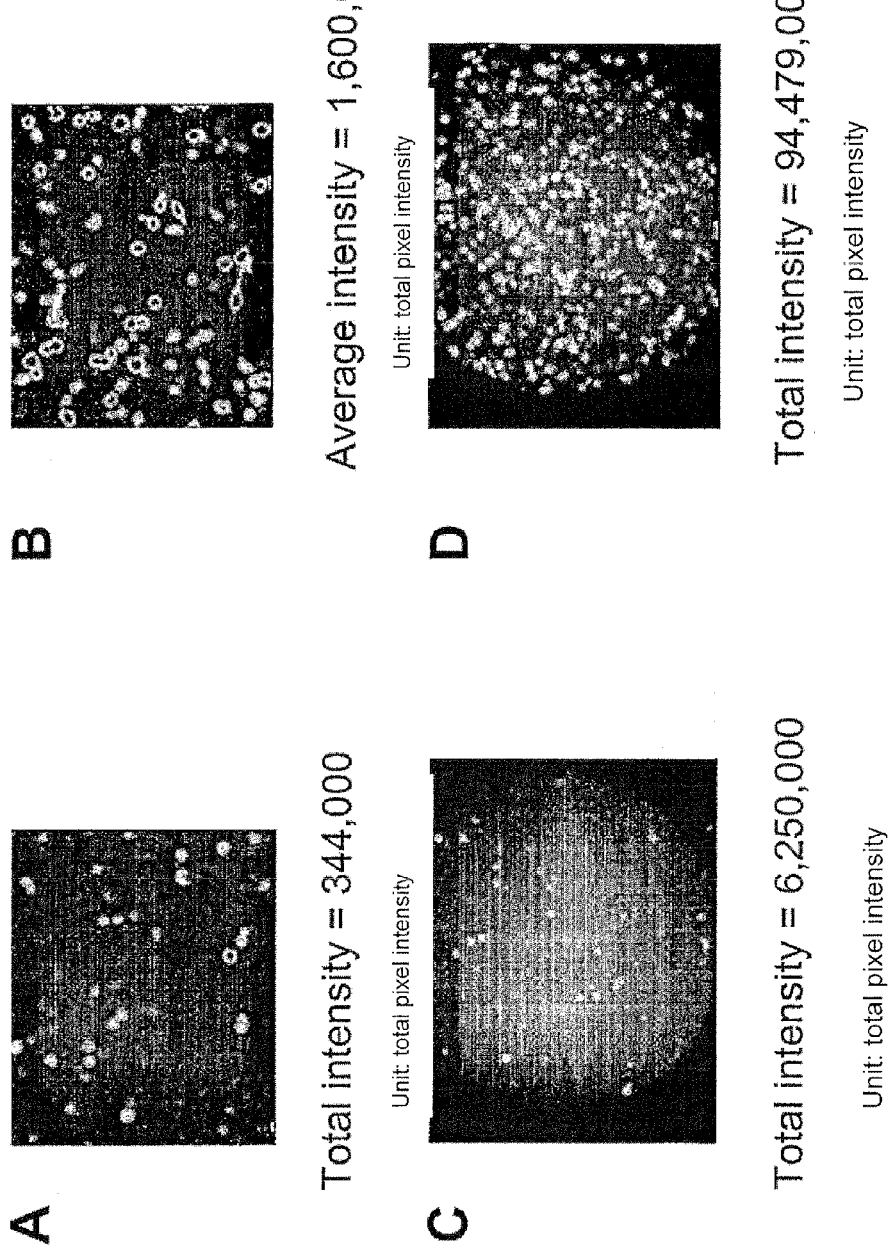
FIG. 3. GFP fluorescence due to protein expression in two different cell types, HeLa (A and B) and Huh7 liver cell line (C and D) using the unmodified vector (A and C) and vector containing the hybrid 3'UTR (B and D).

The expression vector with the hybrid 3'UTR was used in two types of cell lines, HeLa cells which is a cervical cell line (FIGS. 3A and B), and Huh7 which is a liver cell line (FIGS. 3C and D). The cells were grown at standard culture conditions (37° C., 5% $CO_2$) in DMEM medium supplemented with 10% FBS and antibiotics (Gibco BRL, Gaithersburg, Md.). $3\times10^4$ cells per well in 96-well plates were transfected with 1 µg of the original expression vector (FIGS. 3A and C) or the modified vector FIGS. 3B and D). Transfections were performed in serum-free medium using LipofectinAmine 2000 (Gibco) for 5 h, followed by replacing medium with serum-supplemented medium. After approximately 48 hours, the cells were visualized using a fluorescence microscope and the optimal excitation wavelength for GFP of 488 nm and emission wavelength of 503 nm. Images were captured using a camera mounted on top of the microscope. The images were read by an algorithm that quantitated total fluorescence intensities in pixels. FIG. 3 shows the results of the quantitation. The modified vector, i.e. the vector with the hybrid 3'UTR, resulted in an approximately 5-fold increase in the protein expression in HeLa cell line and more than 15-fold increase in protein expression in Huh7 cell line (as evaluated by the GFP expression).

Example 4

A PCR product generated from the modified vector using primers flanking the CMV promoter and the hybrid 3'UTR still leads to efficient transfection and optimum protein expression. HEK293 cells in $3\times10^4$ cells per well in 96-well plates were transfected with 1 µg of the original expression vector (FIG. 4A) or with said PCR product generated from the modified vector (FIG. 4B). Transfections were performed in serum-free medium using LipofectinAmine 2000 (Gibco) for 5 h, followed by replacing medium with serum-supplemented medium. After approximately 72 hours, the cells were visualized using a fluorescence microscope and the optimal excitation wavelength for GFP of 488 nm and emission wavelength of 503 nm. Images were captured using a camera mounted on top of the microscope. The images were read by an algorithm that quantitates total fluorescence intensities in pixels. FIG. 4 also shows the results of the quantitations showing that the GFP expression resulting from the PCR product which contains the hybrid 3'UTR is still as effective as the GFP expression resulting from the original vector.

REFERENCES

Bakheet, T., Frevel, M., Williams, B R, and K. S. Khabar, 2001. APED: Human AU-rich element-containing mRNA database reveals unexpectedly diverse functional repertoire of encoded proteins. *Nucleic Acids Research.* 29:246-254.

Chen, C. Y. and A. D. Shyu. 1994. Selective degradation of early-response-gene mRNAs: functional analyses of sequence features of the AU-rich elements. *Mol Cell Biol* 14: 8471-8482.

Dalphin, M. E., P. A. Stockwell, W. P, Tate, and C. M. Brown. 1999, TransTerm, the translational signal database, extended to include full coding sequences and untranslated regions. *Nucleic Acids Res* 27: 293-294.

Eisenberg, E. and E. Y. Levanon. 2003. Human housekeeping genes are compact. *Trends Genet.* 19(7): 362-365.

Foecking, M. K. and H. Hofstetter. 1986. Powerful and versatile enhancer-promoter unit for mammalian expression vectors. *Gene* 45: 101-105.

Goodwin B. C. and F. M. Rottman. 1992. The 3'-flanking sequence of the bovine growth hormone gene contains novel elements required for efficient and accurate polyadenylation. *J Biol Chem* 267: 16330-16334.

Kobayashi, M., A. Tanaka, Y. Hayashi, and S. Shimamura. 1997. The CMV enhancer stimulates expression of foreign genes from the human BF-1 alpha promoter. *Anal Biochem* 247: 179-181.

Legendre, M. and D. Gautheret. 2003. Sequence determinants in human polyadenylation site selection. *BMC Genomics* 4: 7.

Shaw, G. and R. Kramen. 1986. A conserved AU sequence from the 31 untranslated region of GM-CSF mRNA mediates selective mRNA degradation. *Cell* 46: 659-667.

Wigley, P. L., M. D. Sheets, D. A. Zarkower, M. E. Whitner, and M. Wickens. 1990. Polyadenylation of mRNA: minimal substrates and a requirement for the 2' hydroxyl of the U in AAUAAA. *Mol Cell Biol* 10: 1705-1713.

The invention claimed is:

1. A recombinant nucleic acid comprising a hybrid 3' untranslated region (3'UTR) that comprises a first and a second nucleic acid region, wherein
   (a) said first region is a 3' untranslated region (3'UTR) of a stable eukaryotic mRNA of eukaryotic translation elongation factor 1 alpha 1 (EEF1A1) or is part of the 3'UTR of EEF1A1 mRNA,
   (b) said first region does not contain a polyadenylation signal,
   (c) said second region is derived from the downstream end of an 3' untranslated region of another or the same stable eukaryotic mRNA as in (a), and
   (d) said second region contains a polyadenylation signal, wherein said recombinant nucleic acid has the sequence of SEQ ID NO:3.

2. The recombinant nucleic acid of claim 1, wherein said first region and said second region are in proximity to each other or are adjacent to each other or overlap with each other or one encompasses the other.

3. The recombinant nucleic acid of claim 2, wherein the 3' end of the first region is adjacent to the 5' end of the second region or the 3' end of the second region is adjacent to the 5' end of the first region or the first region is located within the second region.

4. The recombinant nucleic acid of claim 1, wherein the nucleic acid is DNA, RNA, or PNA.

5. An expression vector comprising the recombinant nucleic acid according to claim 1.

6. The expression vector according to claim 5 further comprising a selection marker.

7. The expression vector according to claim 5, wherein the recombinant nucleic acid according to claim 1 further comprises a protein coding sequence that encodes a reporter protein or a therapeutic protein.

8. An isolated host cell comprising the expression vector of claim 5 wherein the expression vector of claim 5 comprises a protein coding sequence, and the host cell transiently or encoded in the expression vector of claim 5.

9. An isolated host cell which is obtained by in vivo injection of the expression vector of claim 5 into a cell, wherein the expression vector of claim 5 comprises a protein coding sequence, and the host cell comprises the expression vector of claim 5 and transiently or encoded in the expression vector of claim 5.

10. A method for obtaining a host cell, comprising the following steps of
    (a) providing an expression vector according to claim 5,
    (b) in vivo injection of the expression vector according to claim 5 into a cell, and
    (c) obtaining the injected cell of step (b).

11. A method for expressing proteins, comprising providing and culturing of the host cell according to claim 8, under conditions allowing transient or stable expression of proteins, and obtaining said expressed proteins.

12. The recombinant nucleic acid of claim 3, wherein the first region is located upstream of the polyadenylation signal of the second region.

13. A recombinant nucleic acid comprising the following components in 5' to 3' direction:
    (a) a promoter sequence,
    (b) a protein coding region sequence, and (c) a hybrid 3'UTR comprising the sequence of SEQ ID NO: 3, which is operably linked to the protein coding sequence of (b).

14. The recombinant nucleic acid according to claim 13, wherein the nucleic acid is a linear DNA molecule and is generated by PCR using at least two primers that specifically hybridize to regions near the 5' end and specifically hybridize to regions near the 3' end of the nucleic acid according to claim 13 which is comprised in an expression vector.

15. A method of producing a nucleic acid in linear form, comprising the following steps of
    (a) providing an expression vector comprising the recombinant nucleic acid according to claim 13,
    (b) providing at least two primers, wherein one primer specifically hybridizes to regions near the 5' end of the nucleic acid according to claim 6, and wherein the other primer specifically hybridizes to regions near the 3' end of the nucleic acid according to claim 13,
    (c) performing a PCR, and
    (d) obtaining the amplification product of step (c).

16. An isolated host cell comprising the recombinant nucleic acid of claim 14, wherein the host cell is capable of transiently or stably expressing the protein encoded by the recombinant nucleic acid of claim 14.

17. An isolated host cell which is obtained by in vivo injection of the recombinant nucleic acid of claim 14 into a cell, wherein the host cell comprises the recombinant nucleic acid of claim 14 and is capable transiently or stably expressing the protein encoded by the recombinant nucleic acid of claim 14.

18. A method for obtaining a host cell, comprising the following steps of
    (a) providing a recombinant nucleic acid of claim 14,
    (b) in vivo injection of the recombinant nucleic acid of claim 14 into a cell, and
    (c) obtaining the injected cell of step (b).

19. A method for expressing proteins, comprising providing and culturing of the host cell according to claim 16, under conditions allowing transient or stable expression of proteins, and obtaining said expressed proteins.

* * * * *

UNITED STATES PATENT AND TRADEMARK OFFICE
CERTIFICATE OF CORRECTION

PATENT NO. : 9,017,965 B2  
APPLICATION NO. : 12/097169  
DATED : April 28, 2015  
INVENTOR(S) : Khalid S. Abu Khabar Page 1 of 4

It is certified that error appears in the above-identified patent and that said Letters Patent is hereby corrected as shown below:

In the specification,

Column 1,  
Line 49, "GNA" should read --gDNA--.

Column 1,  
Line 53, "NA" should read --RNA--.

Column 2,  
Line 14, "NA" should read --mRNA--.

Column 2,  
Line 32, "CMV/Itron" should read --CMV/Intron--.

Column 3,  
Line 2, "an 3," should read --an 3'--.

Column 3,  
Line 9, "3'-UTR" should read --3'UTR--.

Column 3,  
Line 11, "3'UM" should read --3'UTR--.

Column 3,  
Line 22, "(3'-UTR)" should read --(3'UTR)--.

Column 3,  
Line 39, "3," should read --3'--.

Signed and Sealed this  
Twelfth Day of January, 2016

Michelle K. Lee  
*Director of the United States Patent and Trademark Office*

Column 3,
Line 42, "with the" should read --within the--.

Column 3,
Line 56, "preformed" should read --preferred--.

Column 4,
Line 1, "3'UM" should read --3'UTR--.

Column 4,
Line 9, "that ter" should read --that further--.

Column 4,
Line 23, "3'- UTR" should read --3'UTR--.

Column 4,
Line 26, "in 5," should read --in 5'--.

Column 4,
Line 30, "lined" should read --linked--.

Column 4,
Line 53, "37 end" should read --3' end--.

Column 4,
Line 59, "art" should read --art,--.

Column 5,
Line 8, "in 57" should read --in 5'--.

Column 5,
Line 16, "5, end" should read --5'end--.

Column 5,
Line 22, "5, to" should read --5' to--.

Column 5,
Line 36, "3, direction:" should read --3' direction:--.

Column 5,
Line 49, "to 37" should read --to 3'--.

Column 6,
Line 27, "pH 1" should read --pH--.

Column 6,
Line 44, "3'-UTR" should read --3'UTR--.

Column 6,
Lines 62-63, "invitrogen," should read --Invitrogen,--.

Column 6,
Line 66, "USR" should read --UTR--.

Column 8,
Line 16, "(SEAM" should read --(SEM--.

Column 13,
Line 25, "ter" should read --further--.

Column 14,
Line 42, "bGH)" should read --(bGH)--.

Column 15,
Line 2, "PBS" should read --FBS--.

Column 16,
Line 18, "APED:" should read --ARED:--.

Column 16,
Line 22, "A. D." should read --A. B.--.

Column 16,
Line 35, "Goodwin B.C." should read --Goodwin, E.C.--.

Column 16,
Line 41, "BF-1" should read --EF-1--.

Column 16,
Line 47, "the 31" should read --the 3'--.

Column 16,
Line 49, "Whitner," should read --Whitmer,--.

In the claims,

Column 18,
Lines 42-43, "host cell transiently or encoded" should read --host cell is capable of transiently or stably expressing a protein encoded--.

Column 18,
Line 48, "and transiently or encoded" should read --and is capable of transiently or stably expressing a protein encoded--.

Column 20,
Line 9, "the protein" should read --a protein--.

Column 19,
Line 17, "to claim 6" should read --to claim 13--.